United States Patent [19]

Beavers

[11] Patent Number: 4,487,943

[45] Date of Patent: Dec. 11, 1984

[54] CATALYTIC PROCESS FOR THE PREPARATION OF TETRAHYDROPYRAN BY HOMOLOGATION OF TETRAHYDROFURAN

[75] Inventor: William A. Beavers, Longview, Tex.

[73] Assignees: Eastman Kodak Company, Rochester, N.Y.

[21] Appl. No.: 559,986

[22] Filed: Dec. 9, 1983

[51] Int. Cl.³ .............................................. C07D 309/04
[52] U.S. Cl. ..................................... 549/356; 549/346
[58] Field of Search ................................. 549/356, 346

[56] References Cited

U.S. PATENT DOCUMENTS 4,203,908  5/1980  Mueller et al. ...................... 549/356
4,336,195  6/1982  Renga ................................. 549/356

*Primary Examiner*—Nicky Chan
*Attorney, Agent, or Firm*—David E. Cotey; Daniel B.

[57] ABSTRACT

The present invention relates to a catalytic process for the preparation of tetrahydropyran by the homologation of tetrahydrofuran. The process comprises reacting tetrahydrofuran with synthesis gas in the presence of a catalyst system comprising ruthenium, rhodium, and, preferably, a halide promoter.

18 Claims, No Drawings

CATALYTIC PROCESS FOR THE PREPARATION OF TETRAHYDROPYRAN BY HOMOLOGATION OF TETRAHYDROFURAN

DESCRIPTION

The present invention relates to a process for the preparation of tetrahydropyran by the reductive carbonylation (or, homologation) of tetrahydrofuran.

Tetrahydropyran has previously been manufactured by the dehydration of 1,5-pentanediol. See, for example, Ger. Offen. No. 2,503,750 and Ger. Offen. No. 2,509,968, in which aqueous mineral acids were employed as dehydrating agents. A solid catalyst for the same process was described in Ger. Offen. No. 2,930,144. Pentanediol in turn can be prepared by the hydrogenation of glutaric acid or glutaric acid esters. East German Pat. No. 142,050 describes a process for hydrogenating glutaric acid or glutaric anhydride directly to tetrahydropyran by the use of rhenium or technurium catalysts. A platinum catalyst for a related process employing aldehydes as starting materials was reported in U.S.S.R. Pat. No. 534,455.

It is also known that, under homologation conditions, acyclic ethers generate primarily carbonylation products. For example, diethyl ether gives mainly ethyl propionate. By analogy, it would be expected that tetrahydrofuran in a homologation reaction would produce mainly δ-valerolactone.

In contrast to known homologation processes and to known processes for producing tetrahydropyran, it has now been found that tetrahydropyran can be produced by the homologation of tetrahydrofuran by the use of a catalyst system comprising ruthenium and rhodium.

SUMMARY OF THE INVENTION

The present invention provides a process for the preparation of tetrahydropyran. The process comprises reacting tetrahydrofuran with a mixture of carbon monoxide and hydrogen at a temperature of about 100° to 400° C. and a pressure of about 200 to 20,000 psig in the presence of a homogeneous catalyst system comprising ruthenium and rhodium.

DETAILED DESCRIPTION OF THE INVENTION

The present invention relates to a novel process for preparing tetrahydropyran. This invention provides a completely new route to a compound which has been known for a long time. Tetrahydropyran has been thought to have limited utility primarily because of its lack of availability. Its properties are similar to those of tetrahydrofuran and dioxane. Therefore, an attractive commercial route for its production would give rise to its emergence as a good material for use in a variety of areas. Current demand for tetrahydropyran centers around its uses as a solvent for organic reactions and polymer preparations, as monomer or comonomer in the preparation of polyethers, polyesters, or other addition polymers, and as a chemical intermediate in the pharmaceutical industry, especially in the preparation of analgesics.

The process of the present invention comprises reacting tetrahydrofuran with a mixture of carbon monoxide and hydrogen at elevated temperature and pressure in the presence of a homogeneous catalyst system comprising ruthenium and rhodium. In addition to the metallic catalyst components, the catalyst system preferably further comprises a halide promoter.

The metals may be introduced in any form which provides a solution of the metals under the conditions of the reaction. Thus, ruthenium or rhodium powder, ingots, sponges, plates, sheet, wire, precipitates, or coatings on inert or partially inert supports may be used as catalyst sources. However, the rate of reaction will be very sluggish until the metals become dissolved. More usual and convenient sources of the metals include the halides, such as the trifluorides, trichlorides, tribromides, and triiodides; oxides and hydroxides, such as ruthenium dioxide, ruthenium tetraoxide, rhodium dioxide, dirhodium trioxide hydrate, etc.; salts of strong mineral acids, such as ruthenium nitrate, ruthenium phosphate, ruthenium sulfate, rhodium nitrate, rhodium phosphate, rhodium sulfate, etc. Salts of weak aliphatic carboxylic acids, such as the formates, acetates, propionates, butyrates, valerates, and other salts of mono- or polybasic aliphatic carboxylic acids having less than about 20 carbon atoms; salts of weak aromatic carboxylic acids, such as the benzoates, phthalates, naphthanoates, or salts of other mono- or polybasic aromatic acids having less than about 20 carbon atoms; 2,4-pentanedionato derivatives, such as tri(2,4-pentanedionato)ruthenium, tri(2,4-pentanedionato)rhodium, dicarbonyl-2,4-pentanedionato rhodium, or other similar derivatives containing the β-diketonate functionality; carbonyl derivatives such as ruthenium pentacarbonyl, triruthenium dodecacarbonyl, dicarbonyl rhodium chloride, tetrarhodium dodecacarbonyl, hexarhodium hexadecacarbonyl, or other such carbonyls; Group Va complexes such as tris(triphenylphosphine)ruthenium dichloride; tetrakis(triphenylphosphine)ruthenium dichloride, tris(triphenylphosphine)carbonyl ruthenium hydrido chloride, tris(triphenylphosphine)carbonyl ruthenium dihydride, tris(triphenylphosphine)rhodium chloride, carbonyl bis(triphenylphosphine)rhodium chloride, carbonyl tris(triphenylphosphine)rhodium hydride, other similar combinations in which the halogen has been replaced with fluoride, chloride, and iodide, or in which the triphenylphosphine has been replaced with carbonyl groups; etc.

The concentrations of the metals may vary over a wide range, but is to be understood that the rate of formation of tetrahydropyran from tetrahydrofuran is greatest at higher metal concentrations. Thus, any concentration of total metals (i.e., the total concentration of rhodium and ruthenium in the catalyst system) greater than about $10^{-6}$ molar is suitable, with the upper limit being determined by the solubility of active catalyst components under reaction conditions. Preferably, the concentration of total metals is in the range of about $10^{-6}$ to 10 molar. A more preferred concentration is about $10^{-4}$ to 5 molar (e.g., about $10^{-2}$ to 2 molar).

An important consideration in the optimal production of tetrahydropyran from tetrahydrofuran by the process of the present invention is the ratio of rhodium to ruthenium. While any combination will function in the process of the present invention, there is an optimal ratio of the two metals which gives the best combination of rate and selectivity. At high rhodium concentrations, δ-valerolactone apears as a contaminant because of inefficient hydrogenation; at high ruthenium concentrations, n-butanol and n-valeric acid appear as contaminants due to hydrogenolysis. Also, at high ruthenium concentrations, a diminution in rate is observed. Thus, the preferred ruthenium: rhodium molar ratio is in the range of about 1:10 to 10:1. More preferably, the range of ruthenium:rhodium is about 1:2 to 5:1 (most preferably, about 1:1 to 3:1).

In order to achieve optimum reaction rates and selectivities, a halide promoter is included in the reaction system in preferred embodiments of the present invention. While any halide will function (i.e., fluoride, chloride, bromide, and iodide), iodide is the halide of choice. The halide may be introduced in any convenient form, including molecular halogen, hydrogen halide, alkali metal halide, alkaline earth halide, Lewis acid halides, organic halides, such as alkyl halides wherein the alkyl group contains less than about 20 carbon atoms, etc. Specific preferred sources of halide include iodine, hydrogen iodide, lithium iodide, sodium iodide, potassium iodide, cesium iodide, magnesium iodide, calcium iodide, strontium iodide, barium iodide, aluminum iodide, titanium iodide, zinc iodide, methyl iodide, ethyl iodide, propyl iodide, butyl iodide, etc. Especially preferred sources of halide include methyl iodide, iodine, hydrogen iodide, and lithium iodide, among others.

The concentration of the halide promoter can also vary over a wide range. Suitable concentrations of halide are dependent upon the concentration of the metal catalyst components. The molar ratio of halide:total metals (i.e., Rh+Ru) preferably falls in the range of about 5:1 to 100:1. A more preferable range is about 10:1 to 50:1, and the most preferred range is about 15:1 to 45:1. Of course, if the total metals concentration is in the upper limits of the range given above, the halide:metals ratio will tend to be relatively small. Likewise, if the total metals concentration is in the lower limits of the range given above, the halide:metals ratio will tend to be in the upper limits of its preferred values. In this manner, the optimal operation of the catalyst can be ensured.

In accordance with the process of the present invention, tetrahydrofuran is reacted in the presence of the above-described catalyst system with a mixture of carbon monoxide and hydrogen. This gas mixture typically comprises synthesis gas in which the molar ratio of hydrogen:carbon monoxide is about 1:10 to 10:1. In preferred embodiments, the $H_2$:CO molar ratio will be about 1:2 to 5:1 (e.g., about 1:2 to 2:1).

The reaction is conducted in the presence of a suitable solvent system. Typically, the solvent will comprise the tetrahydrofuran reactant in excess. However, other solvents which are inert to the reaction conditions can also be employed. Such solvents include, for example, sulfolane; aromatic and aliphatic hydrocarbons having less than about 20 carbon atoms, such as hexane, benzene, xylene, toluene, etc.; n-methylpyrrolidone; etc. Other suitable solvents will be apparent to the person of ordinary skill in the art.

The reaction is conducted at elevated temperature and pressure. The preferred range of temperature is about 100° to 400° C. A more preferred range is about 150° to 330° C. (e.g., about 200° to 250° C.). The pressure under which the reaction is conducted is preferably about 200 to 20,000 psig. A more preferred range is about 1,000 to 10,000 psig (e.g., about 2000 to 5,000 psig). The conversion of tetrahydrofuran to tetrahydropyran can occur outside of the stated conditions. However, at higher temperatures, the formation of by-products becomes excessive, while at lower temperatures, the rates are too small to be of value. Moreover, the rate of reaction is also adversely affected at pressures lower than those described above, while at high pressure, economic and safety considerations become important.

This invention will be further illustrated by the following Examples although it will be understood that these Examples are included merely for purposes of illustration and are not intended to limit the scope of the invention.

EXAMPLE 1

A 300-ml Hastelloy C autoclave was flushed with nitrogen and was then charged with 2.5 millimoles of ruthenium(III)tris(2,4-pentanedionate), 0.5 millimole of iodorhodium(I)tris(triphenylphosphine), 120 millimoles of iodomethane, and 100 ml of tetrahydrofuran. The autoclave head was bolted on, and the contents were stirred rapidly while being subjected to a pressure of 3500 psig of synthesis gas having a $H_2$:CO molar ratio of 1.5:1. The autoclave was heated to 220° C., and the pressure was adjusted to 4900 psig. The pressure was maintained at that level by periodic refilling from a gas reservoir. During the one-hour reaction time, the total pressure drop was 2200 psig. After the reaction was completed, the reaction vessel was cooled and vented, and the contents were analyzed. Total conversion of starting material was 26.1 percent. The yields of the products were as follows: 58.2 percent tetrahydropyran, 3.7 percent butane, 2.2 percent n-butyl alcohol, 4.8 percent n-butyl acetate, 8.5 percent acetic acid, 9.2 percent n-valeric acid, 2.6 percent n-butanal, and 10.8 percent other products, including mostly higher cyclic ethers.

EXAMPLE 2

Example 1 was repeated except the catalyst consisted of 2 millimoles of ruthenium(III)tris(2,4-pentanedionate), 1 millimole of iodorhodium(I)tris(triphenylphosphine), and 60 millimoles of iodine. The average pressure of the run was 4200 psig and the total pressure drop in 1 hour was 4000 psig. Analysis of the reaction products revealed a tetrahydrofuran conversion of 38.7 percent. The yields of the products were: 78.0 percent tetrahydropyran, 1.7 percent butane, 3.4 percent butyl alcohol, 3.2 percent 2-methyltetrahydrofuran, 1.2 percent hexamethylene oxide, 9.5 percent linear polyethers, and 3.0 percent miscellaneous.

EXAMPLE 3

Example 2 was repeated except the ruthenium source was tris(triphenylphosphine)ruthenium(II)dichloride. The average pressure of the run was 4500 psig and the total pressure drop was 4200 psig. Analysis of the contents of the autoclave at the conclusion of the run revealed a 31.5 percent tetrahydrofuran conversion. The yields of the products were: 80.5 percent tetrahydropyran, 1.2 percent butane, 0.8 percent butyl alcohol, 2.6 percent hexamethylene oxide, 9.6 percent linear polyethers, and 5.3 percent miscellaneous.

EXAMPLE 4

Example 2 was repeated except that the ruthenium source was ruthenium trichloride hydrate and the rhodium source was rhodium trichloride hydrate. The average pressure of the run was 4500 psig and the total pressure drop was 3000 psig. Analysis of the contents of the autoclave at the conclusion of the run revealed a 34.8 percent tetrahydrofuran conversion. The yields of the products were: 81.1 percent tetrahydropyran, 2.1 percent butane, 1.5 percent n-butyl alcohol, 1.1 percent hexamethylene oxide, 7.9 percent linear polyethers, and 6.3 percent miscellaneous.

These Examples demonstrate the excellent selectivity to tetrahydropyran provided by the catalytic process of the present invention. In addition, the process of the present invention provides the desired product at advantageous rates.

While the invention has been described in detail with particular reference to preferred embodiments thereof, it will be understood that variations and modifications can be effected within the spirit and scope of the invention.

I claim:

1. A process for the preparation of tetrahydropyran which comprises reacting tetrahydrofuran with a mixture of carbon monoxide and hydrogen at a temperature of about 100° to 400° C. and a pressure of about 200 to 20,000 psig in the presence of a homogeneous catalyst system comprising ruthenium and rhodium.

2. The process of claim 1 wherein said catalyst system further comprises a halide promoter.

3. The process of claim 2 wherein said halide promoter comprises iodide.

4. The process of claim 1 wherein the molar ratio of ruthenium:rhodium is about 1:10 to 10:1.

5. The process of claim 4 wherein the total concentration of catalyst metals in the system is about $10^{-6}$ to 10 molar.

6. The process of claim 2 wherein the molar ratio of halide to total catalyst metals is about 5:1 to 100:1.

7. The process of claim 1 wherein the molar ratio of hydrogen:carbon monoxide is about 1:10 to 10:1.

8. A process for the preparation of tetrahydropyran which comprises reacting tetrahydrofuran with a mixture of hydrogen and carbon monoxide having a $H_2:CO$ molar ratio of about 1:10 to 10:1 at a temperature of about 100° to 400° C. and a pressure of about 200 to 20,000 psig in the presence of a homogeneous catalyst system comprising ruthenium and rhodium, the Ru:Rh molar ratio being about 1:10 to 10:1 and the total catalyst metals concentration being about $10^{-6}$ to 10 molar, said catalyst system further comprising a halide promoter, with the molar ratio of halide:total catalyst metals being about 5:1 to 100:1.

9. The process of claim 8 wherein said halide promoter comprises iodide.

10. The process of claim 8 wherein the $H_2:CO$ molar ratio is about 1:2 to 5:1.

11. The process of claim 8 wherein the Ru:Rh molar ratio is about 1:2 to 5:1.

12. The process of claim 8 wherein the total catalyst metals concentration is about $10^{-4}$ to 5 molar.

13. The process of claim 9 wherein the molar ratio of iodide:total catalyst metals is about 10:1 to 50:1.

14. A process for the preparation of tetrahydropyran which comprises reacting tetrahydrofuran with a mixture of hydrogen and carbon monoxide having a $H_2:CO$ molar ratio of about 1:2 to 5:1 at a temperature of about 100° to 400° C. and a pressure of about 200 to 20,000 psig in the presence of a homogeneous catalyst system comprising ruthenium, rhodium, and an iodide promoter, the Ru:Rh molar ratio being about 1:2 to 5:1, the total catalyst metals concentration being about $10^{-4}$ to 5 molar, and the molar ratio of iodide:total catalyst metals being about 10:1 to 50:1.

15. The process of claim 14 wherein the $H_2:CO$ molar ratio is about 1:2 to 2:1.

16. The process of claim 14 wherein the Ru:Rh molar ratio is about 1:1 to 3:1.

17. The process of claim 14 wherein the total catalyst metals concentration is about $10^{-2}$ to 2 molar.

18. The process of claim 14 wherein the molar ratio of iodide:total catalyst metals is about 15:1 to 45:1.

* * * * *